United States Patent [19]

Collier et al.

[11] Patent Number: 5,601,827
[45] Date of Patent: Feb. 11, 1997

[54] DIPHTHERIA TOXIN VACCINES

[75] Inventors: R. John Collier, Wellesley Hills; Kevin Killeen, Milton; John Mekalanos, Cambridge, all of Mass.

[73] Assignee: President and Fellows of Harvard College, Cambridge, Mass.

[21] Appl. No.: 447,413

[22] Filed: May 23, 1995

Related U.S. Application Data

[63] Continuation of Ser. No. 227,196, Apr. 13, 1994, abandoned, which is a continuation of Ser. No. 901,712, Jun. 18, 1992, abandoned.

[51] Int. Cl.$^6$ ............ A61K 39/05; A61K 48/00; C12N 15/31
[52] U.S. Cl. .............. 424/190.1; 424/192.1; 424/238.1; 424/93.2; 424/832; 435/172.3; 435/69.1; 435/69.7; 435/194; 435/252.3; 435/252.31; 435/252.32; 435/252.33; 435/254.11; 435/320.1
[58] Field of Search ............... 435/69.1, 69.7, 435/240.1, 252.3, 252.31, 252.32, 194, 254.11; 424/93.2, 190.1, 192.1, 238.1, 236.1; 536/23.2, 23.7; 514/44

[56] References Cited

U.S. PATENT DOCUMENTS

| | | | |
|---|---|---|---|
| 4,709,017 | 11/1987 | Collier et al. | 530/350 |
| 4,950,740 | 8/1990 | Greenfield et al. | 530/350 |
| 5,149,532 | 9/1992 | Brunell | 424/89 |

OTHER PUBLICATIONS

Cieplak et al (1988) Proc. Nat. Acad Sci, USA 85 4667–4671.
Barbieri, et al., Expression of a Mutant, Full–Length Form of Diphtheria Toxin in *Escherichia coli*, Infection and Immunity, 55:1647–1651, 1987.
Fisher, et al., Construction and Expression of Plasmids Containing Mutated Diphtheria Toxin A–Chain–Coding Sequences, Infection and Immunity, 59:3562–3565, 1991.
Giannini, et al., The amino–acid sequence of two non–toxic mutants of diphtheria toxin: CRM45 and CRM197, Nucleic Acids Research, 12:4063–4069, 1984.

Greenfield, et al., Mutations in Diphtheria Toxin Separate Binding from Entry and Amplify Immunotoxin Selectivity, Science, 238:536–539, 1987.
Greenfield, et al., Nucleotide sequence of the structural gene for diphtheria toxin carried by corynebacteriophageβ, PNAS, 80:6853–6857, 1983.
Locht, et al., Identification of amino acid residues essential for the enzymatic activities of pertussis toxin, PNAS, 86:3075–3079, 1989.
Tweten, et al., Diphtheria Toxin, Effect of Substituting Aspartic Acid For Glutamic Acid 148 on Adp–Ribosyltyransferase Activity, The J. of Biol. Chem., 260:10392–10394, 1985.
Maxwell, et al., Cloning, Sequence Determination, and Expression in Transfected Cells of the Coding Sequence of the tox 176 Attenuated Diphtheria Toxin A Chain, Mol. and Cell. Bio., 7:1576–1579, 1987.
Tang, et al., Genetic immunization is a simple method for eliciting an immune response, Nature, 356:152–154 1973.
Uchida, et al., Mutation in the Structural Gene for Diphtheria Toxin carried by Temperate Phage β, Nature New Biology, 33:8–11, 1971.
Uchida, et al., Diphtheria Toxin and Related Proteins, The J. of Biol. Chem., 248:3838–3844, 1973.
Ward, diphtheria toxin: a novel cytocidal enzyme, Trends Biochem, 12:28–30, 1987.
Wilson, et al., Active–Site of Diphtheria Toxin: Effects of Replacing Glutamic Acid–148 with Aspartic Acid, Glutamine, or Serine, Biochem., 29:8643–8651, 1990.
Choe, et al., The crystal structure of diphtheria toxin, Nature, 357:216–222, 1992.
Lukačet al (1988) Infect. Immun. 56: 3095–3098.

*Primary Examiner*—Robert A. Wax
*Assistant Examiner*—Gabriele E. Bugaisky
*Attorney, Agent, or Firm*—Fish & Richardson P.C.

[57] ABSTRACT

A DNA encoding an immunologically cross-reactive form of diphtheria toxin Fragment A, wherein the codons corresponding to Val-147 and Glu-148 of naturally-occurring diphtheria toxin are deleted from the DNA.

19 Claims, 4 Drawing Sheets

```
CCGGCGTTGC GTATCCAGTG GCTACACTCA GGTTGTAATG ATTGGGATGA TGTACCTGAT    60

CTGAGAGCGA TTAAAAACTC ATTGAGGAGT AGGTCCCGAT TGGTTTTTGC TAGTGAAGCT   120

TAGCTAGCTT TCCCCATGTA ACCAATCTAT CAAAAAGGG CATTGATTTC AGAGCACCCT   180

TATAATTAGG ATAGCTTTAC CTAATTATTT TATGAGTCCT GGTAAGGGGA TACGTTGTGA   240

GCAGAAAACT GTTTGCGTCA ATCTTAATAG GGGCGCTACT GGGGATAGGG GCCCCACCTT   300

CAGCCCATGC A                                                         311
```

```
GGC GCT GAT GAT GTT GTT GAT TCT TCT AAA TCT TTT GTG ATG GAA AAC    359
Gly Ala Asp Asp Val Val Asp Ser Ser Lys Ser Phe Val Met Glu Asn
1           5                   10                  15

TTT TCT TCG TAC CAC GGG ACT AAA CCT GGT TAT GTA GAT TCC ATT CAA    407
Phe Ser Ser Tyr His Gly Thr Lys Pro Gly Tyr Val Asp Ser Ile Gln
            20                  25                  30

AAA GGT ATA CAA AAG CCA AAA TCT GGT ACA CAA GGA AAT TAT GAC GAT    455
Lys Gly Ile Gln Lys Pro Lys Ser Gly Thr Gln Gly Asn Tyr Asp Asp
        35                  40                  45

GAT TGG AAA GGG TTT TAT AGT ACC GAC AAT AAA TAC GAC GCT GCG GGA    503
Asp Trp Lys Gly Phe Tyr Ser Thr Asp Asn Lys Tyr Asp Ala Ala Gly
    50                  55                  60

TAC TCT GTA GAT AAT GAA AAC CCG CTC TCT GGA AAA GCT GGA GGC GTG    551
Tyr Ser Val Asp Asn Glu Asn Pro Leu Ser Gly Lys Ala Gly Gly Val
65              70                  75                  80

GTC AAA GTG ACG TAT CCA GGA CTG ACG AAG GTT CTC GCA CTA AAA GTG    559
Val Lys Val Thr Tyr Pro Gly Leu Thr Lys Val Leu Ala Leu Lys Val
            85                  90                  95

GAT AAT GCC GAA ACT ATT AAG AAA GAG TTA GGT TTA AGT CTC ACT GAA    647
Asp Asn Ala Glu Thr Ile Lys Lys Glu Leu Gly Leu Ser Leu Thr Glu
            100                 105                 110

CCG TTG ATG GAG CAA GTC GGA ACG GAA GAG TTT ATC AAA AGG TTC GGT    695
Pro Leu Met Glu Gln Val Gly Thr Glu Glu Phe Ile Lys Arg Phe Gly
            115                 120                 125

GAT GGT GCT TCG CGT GTA GTG CTC AGC CTT CCC TTC GCT GAG GGG AGT    743
Asp Gly Ala Ser Arg Val Val Leu Ser Leu Pro Phe Ala Glu Gly Ser
        130                 135                 140

TCT AGC GTT GAA TAT ATT AAT AAC TGG GAA CAG GCG AAA GCG TTA AGC    791
Ser Ser Val Glu Tyr Ile Asn Asn Trp Glu Gln Ala Lys Ala Leu Ser
145             150                 155                 160
```

FIG. 1A

```
GTA GAA CTT GAG ATT AAT TTT GAA ACC CGT GGA AAA CGT GGC CAA GAT
Val Glu Leu Glu Ile Asn Phe Glu Thr Arg Gly Lys Arg Gly Gln Asp    839
            165                 170                 175

GCG ATG TAT GAG TAT ATG GCT CAA GCC TGT GCA GGA AAT CGT GTC AGG
Ala Met Tyr Glu Tyr Met Ala Gln Ala Cys Ala Gly Asn Arg Val Arg    887
            180                 185                 190

CGA TCA GTA GGT AGC TCA TTG TCA TGC ATA AAT CTT GAT TGG GAT GTC
Arg Ser Val Gly Ser Ser Leu Ser Cys Ile Asn Leu Asp Trp Asp Val    935
            195                 200                 205

ATA AGG GAT AAA ACT AAG ACA AAG ATA GAG TCT TTG AAA GAG CAT GGC
Ile Arg Asp Lys Thr Lys Thr Lys Ile Glu Ser Leu Lys Glu His Gly    983
            210                 215                 220

CCT ATC AAA AAT AAA ATG AGC GAA AGT CCC AAT AAA ACA GTA TCT GAG
Pro Ile Lys Asn Lys Met Ser Glu Ser Pro Asn Lys Thr Val Ser Glu   1031
225                 230                 235                 240

GAA AAA GCT AAA CAA TAC CTA GAA GAA TTT CAT CAA ACG GCA TTA GAG
Glu Lys Ala Lys Gln Tyr Leu Glu Glu Phe His Gln Thr Ala Leu Glu   1079
            245                 250                 255

CAT CCT GAA TTG TCA GAA CTT AAA ACC GTT ACT GGG ACC AAT CCT GTA
His Pro Glu Leu Ser Glu Leu Lys Thr Val Thr Gly Thr Asn Pro Val   1127
            260                 265                 270

TTC GCT GGG GCT AAC TAT GCG GCG TGG GCA GTA AAC GTT GCG CAA GTT
Phe Ala Gly Ala Asn Tyr Ala Ala Trp Ala Val Asn Val Ala Gln Val   1175
            275                 280                 285

ATC GAT AGC GAA ACA GCT GAT AAT TTG GAA AAG ACA ACT GCT GCT CTT
Ile Asp Ser Glu Thr Ala Asp Asn Leu Glu Lys Thr Thr Ala Ala Leu   1223
            290                 295                 300

TCG ATA CTT CCT GGT ATC GGT AGC GTA ATG GGC ATT GCA GAC GGT GCC
Ser Ile Leu Pro Gly Ile Gly Ser Val Met Gly Ile Ala Asp Gly Ala   1271
305                 310                 315                 320

GTT CAC CAC AAT ACA GAA GAG ATA GTG GCA CAA TCA ATA GCT TTA TCG
Val His His Asn Thr Glu Glu Ile Val Ala Gln Ser Ile Ala Leu Ser   1319
            325                 330                 335

TCT TTA ATG GTT GCT CAA GCT ATT CCA TTG GTA GGA GAG CTA GTT GAT
Ser Leu Met Val Ala Gln Ala Ile Pro Leu Val Gly Glu Leu Val Asp   1367
            340                 345                 350

ATT GGT TTC GCT GCA TAT AAT TTT GTA GAG AGT ATT ATC AAT TTA TTT
Ile Gly Phe Ala Ala Tyr Asn Phe Val Glu Ser Ile Ile Asn Leu Phe   1415
            355                 360                 365

CAA GTA GTT CAT AAT TCG TAT AAT CGT CCC GCG TAT TCT CCG GGG CAT
Gln Val Val His Asn Ser Tyr Asn Arg Pro Ala Tyr Ser Pro Gly His   1463
            370                 375                 380

AAA ACG CAA CCA TTT CTT CAT GAC GGG TAT GCT GTC AGT TGG AAC ACT
Lys Thr Gln Pro Phe Leu His Asp Gly Tyr Ala Val Ser Trp Asn Thr   1511
385                 390                 395                 400

GTT GAA GAT TCG ATA ATC CGA ACT GGT TTT CAA GGG GAG AGT GGG CAC
Val Glu Asp Ser Ile Ile Arg Thr Gly Phe Gln Gly Glu Ser Gly His   1559
            405                 410                 415
```

FIG. 1B

```
GAC ATA AAA ATT ACT GCT GAA AAT ACC CCG CTT CCA ATC GCG GGT GTC      1607
Asp Ile Lys Ile Thr Ala Glu Asn Thr Pro Leu Pro Ile Ala Gly Val
            420                 425                 430

CTA CTA CCG ACT ATT CCT GGA AAG CTG GAC GTT AAT AAG TCC AAG ACT      1655
Leu Leu Pro Thr Ile Pro Gly Lys Leu Asp Val Asn Lys Ser Lys Thr
            435                 440                 445

CAT ATT TCC GTA AAT GGT CGG AAA ATA AGG ATG CGT TGC AGA GCT ATA      1703
His Ile Ser Val Asn Gly Arg Lys Ile Arg Met Arg Cys Arg Ala Ile
            450                 455                 460

GAC GGT GAT GTA ACT TTT TGT CGC CCT AAA TCT CCT GTT TAT GTT GGT      1751
Asp Gly Asp Val Thr Phe Cys Arg Pro Lys Ser Pro Val Tyr Val Gly
465                 470                 475                 480

AAT GGT GTG CAT GCG AAT CTT CAC GTG GCA TTT CAC AGA AGC AGC TCG      1799
Asn Gly Val His Ala Asn Leu His Val Ala Phe His Arg Ser Ser Ser
                485                 490                 495

GAG AAA ATT CAT TCT AAT GAA ATT TCG TCG GAT TCC ATA GGC GTT CTT      1847
Glu Lys Ile His Ser Asn Glu Ile Ser Ser Asp Ser Ile Gly Val Leu
            500                 505                 510

GGG TAC CAG AAA ACA GTA GAT CAC ACC AAG GTT AAT TCT AAG CTA TCG      1895
Gly Tyr Gln Lys Thr Val Asp His Thr Lys Val Asn Ser Lys Leu Ser
        515                 520                 525

CTA TTT TTT GAA ATC AAA AGC TGAAAGGTAG TGGGGTCGTG TGCCGG            1942
Leu Phe Phe Glu Ile Lys Ser
        530             535
```

DIPHTHERIA TOXIN VACCINES

The invention described in this application was made at least in part during work funded by Public Health Service Grants AI-22021 and AI22848 from the National Institute of Allergy and Infectious Diseases. The U.S. Government has certain rights in this invention.

This is a continuation of application Ser. No. 08/227,196, filed Apr. 13, 1994, now abandoned which is a continuation of application Ser. No. 07/901,712, filed Jun. 18, 1992, now abandoned.

BACKGROUND OF THE INVENTION

This invention relates to vaccines which protect against diphtheria toxin.

Diphtheria toxin (DT) is a protein exotoxin produced by the bacterium *Corynebacteria diphtheria*. The DT molecule is produced as a single polypeptide that is readily nicked to form two subunits linked by a disulfide bond, Fragment A (N-terminal ~21K) and Fragment B (C-terminal ~37K), as a result of cleavage at residue 190, 192, or 193 (Moskaug, et al., *Biol Chem* 264:15709–15713, 1989; Collier et al., *Biol Chem*, 246:1496–1503, 1971). Fragment A is the catalytically active portion of DT. It is an NAD-dependent ADP-ribosyltransferase which specifically targets a protein synthesis factor termed elongation factor 2 (EF-2), thereby inactivating EF-2 and shutting down protein synthesis in the intoxicated cell. Fragment B of DT possesses a receptor-binding domain which recognizes and binds the toxin molecule to a particular receptor structure found on the surfaces of many types of mammalian cells. Once DT is bound to the cell via this receptor structure, the receptor/DT complex is taken up by the cell via receptor-mediated endocytosis. A second functional region on Fragment B acts to translocate DT across the membrane of the endocytic vesicle, releasing catalytically active Fragment A into the cytosol of the cell. A single molecule of Fragment A is sufficient to inactivate the protein synthesis machinery in a given cell.

Immunity to a bacterial toxin such as DT may be acquired naturally during the course of an infection, or artificially by injection of a detoxified form of the toxin (a toxoid) (Germanier, ed., *Bacterial Vaccines*, Academic Press, Orlando, Fla., 1984). Toxoids have traditionally been prepared by chemical modification of native toxins (e.g., with formalin or formaldehyde (Lingood et al., *Brit. J. Exp. Path.* 44:177, 1963)), rendering them nontoxic while retaining an antigenicity that protects the vaccinated animal against subsequent challenges by the natural toxin: an example of a chemically-inactivated DT is that described by Michel and Dirkx (*Biochem. Biophys. Acta* 491:286–295, 1977), in which Trp-153 of Fragment A is the modified residue. However, such a chemically modified toxin may occasionally lose the added chemical group or groups, and revert to its active, toxic form, so that its use as a vaccine poses a possible risk to the recipient.

Another avenue for producing toxoids is by the use of genetic techniques. A *Corynebacterium diphtheriae* mutant, CRM-197 (Uchida et al., *J. Biol. Chem.* 248:3838–3844, 1973; Uchida, et al., *Nature* 233:8–11, 1971) (CRM standing for "cross-reacting material") was generated by random mutagenesis and shown to contain an enzymatically inactive DT protein corresponding sufficiently to the natural toxin to produce an anti-DT immune response. Collier et al. (U.S. Pat. No. 4,709,017; herein incorporated by reference) discloses a genetically engineered diphtheria toxin mutant that bears a deletion mutation at Glu-148 of diphtheria toxin. Glu-148 was originally identified as an active-site residue by photoaffinity labelling (Carroll et al., *Proc. Natl. Acad. Sci. USA* 81:3307, 1984; Carroll et al. *Proc. Natl. Acad. Sci. USA* 82:7237, 1985; Carroll et al., *J. Biol. Chem.* 262:8707, 1987). Substitution of Asp, Gln or Ser at this site diminishes enzymatic and cytotoxic activities by 2–3 orders of magnitude, showing that the spatial location and chemical nature of the Glu-148 side-chain greatly affects these activities (Carroll et al., *J. Biol. Chem.* 262:8707, 1987; Tweten et al., *J. Biol. Chem.* 260:10392, 1985; Douglas et al., *J. Bacteriol.* 169:4967, 1987). Similarly, Greenfield et alo (U.S. Pat. No. 4,950,740; herein incorporated by reference) discloses genetically engineered mutant forms of DT in which the Glu-148 residue is deleted or replaced with Asn, and the Ala-158 residue is replaced with Gly. The DNA sequence and corresponding amino acid sequence of wild-type diphtheria toxin DNA are set forth in FIG. 1 (SEQ ID NO:1).

SUMMARY OF THE INVENTION

A recent approach to vaccination utilizes live, genetically engineered microorganisms (cells or viruses) expressing mutant toxin genes. Because live vaccines proliferate in the vaccinee, their genes, including those encoding a genetically engineered toxoid, can in theory mutate over time within the vaccinee. If such a spontaneous mutation causes a genetically engineered toxoid to revert to toxicity, illness and/or death of the vaccinee can result. Applicants have discovered that the DT Glu-148 deletion mutant disclosed in Collier et al., U.S. Pat. No. 4,709,017, a strong candidate for a genetically engineered diphtheria toxoid, carries a small but possibly significant risk of reversion to partial toxicity. They have furthermore discovered ways to reduce this risk without unduly compromising the antigenicity or stability of the resulting polypeptide. The toxoids of the invention, and the DNA which encodes them, carry significantly less risk of reversion than does the Collier et al. Glu-148 deletion mutant, and so are substantially better candidates for using in a live, genetically engineered vaccine cell that is capable of proliferating in the vaccinee.

Figure 1C:
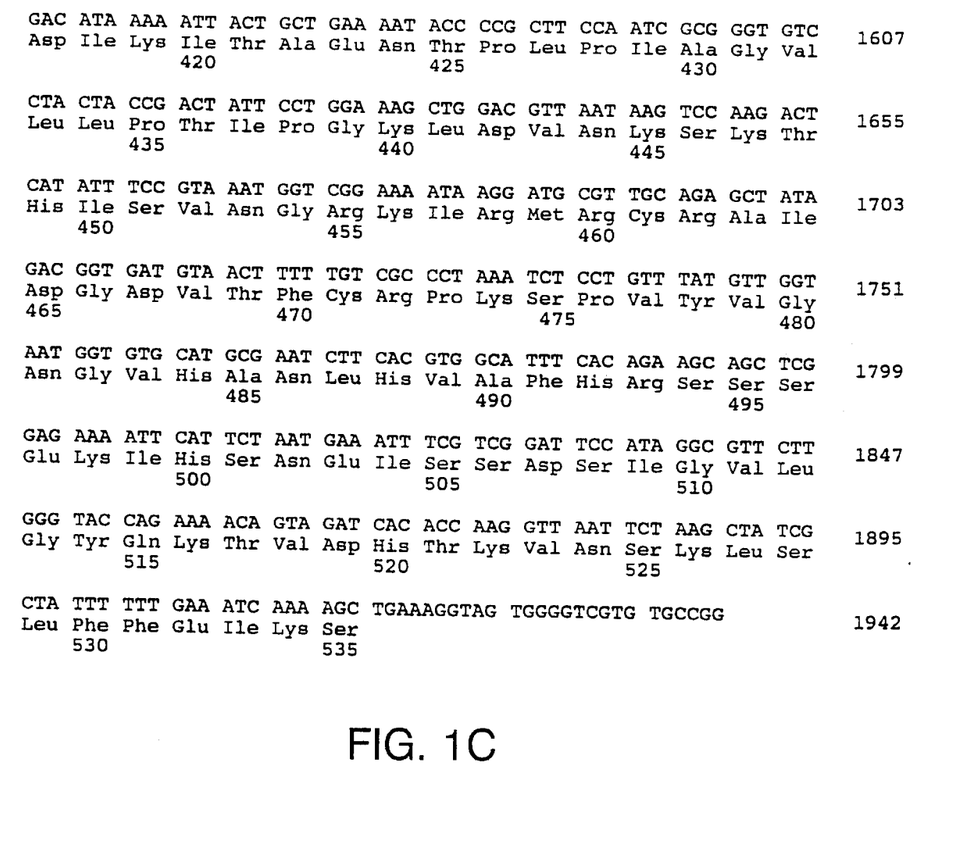
FIG. 1 is a representation of the nucleotide sequence and corresponding amino acid sequence of wild-type diphtheria toxin encoding DNA (SEQ ID NO:1).

The invention features a DNA encoding an immunologically cross-reactive form of diphtheria toxin Fragment A, or encoding both Fragment A and Fragment B, wherein the codons corresponding to Val-147 and Glu-148 (FIG. 1; SEQ ID NO:1) of naturally-occurring diphtheria toxin are absent from the DNA. In addition, a codon corresponding to a third amino acid residue of the naturally occurring toxin can be deleted or altered to encode an amino acid residue different from that of the naturally occurring toxin, the presence of the third amino acid residue of the naturally occurring toxin being essential for the full toxic activity of the naturally occurring toxin. The third amino acid residue may be in the Fragment A portion of diphtheria toxin, in which case the third amino acid residue of the naturally occurring toxin may be, for example, Gly-52, Gly-79, Gly-128, Ala-158, or Glu-162. The third amino acid residue may instead be in the Fragment B portion of diphtheria toxin, the third amino acid residue of the naturally occurring toxin being, for example, Glu-349, Asp-352, or Ile-364. Preferably, the codon corresponding to Glu-142 is absent or is altered to encode an amino acid other than Glu, or all of the codons from Glu-142 to Glu-148, inclusive, are absent. By "naturally occurring" is meant wild-type diphtheria toxin having the amino acid sequence shown in FIG. 1 (SEQ ID NO:1). By the "full toxic activity" of the naturally occurring toxin is meant 100% of the ability of wild-type diphtheria toxin to attach to, penetrate, and kill cells, as measured in a standard cell-killing assay, as described below.

The invention also includes vectors (i.e., plasmids, phages and viruses) including DNA sequences encoding the Fragment A variants described herein. Expression of a diphtheria toxoid polypeptide of the invention is under the control of a heterologous promoter, and/or the expressed amino acids are linked to a signal sequence. By "heterologous promoter" is meant a promoter region that is not identical to the promoter region found in a naturally occurring diphtheria toxin gene. The promoter region is a segment of DNA 5' to the transcription start site of a gene, to which RNA polymerase binds before initiating transcription of the gene. An essentially pure preparation of the nucleic acid of the invention is a preparation containing the nucleic acid of the invention, and which is substantially free of other nucleic acid molecules with which a nucleic acid encoding diphtheria toxin is naturally associated in Corynebacterium. A DNA encoding a diphtheria toxoid of the invention can be contained in a cell, or a homogeneous population of cells, preferably a *B. subtilis*, Bacillus Calmette-Guerin (BCG), *Salmonella sp.*, *Vibrio cholerae*, *Corynebacterium diphtheria*, Listeriae, Yersiniae, Streptococci, or *E. coli* cell. The cell is preferably capable of expressing the diphtheria toxoid polypeptide of the invention.

Diphtheria toxoids that are "immunologically cross-reactive", as that term is used herein, possess at least one antigenic determinant in common with naturally occurring diphtheria toxin, so that they are each bound by at least one antibody with specificity for naturally occurring diphtheria toxin. A "diphtheria toxoid of the invention", as defined herein, refers to a diphtheria toxoid that is immunologically cross-reactive with naturally occurring diphtheria toxin, and which possesses one of the modifications exemplified or claimed herein. An "immunologically cross-reactive form of diphtheria toxin Fragment A" encompasses a diphtheria toxoid polypeptide that is immunologically cross-reactive, and retains at least 40% homology, with naturally occurring Fragment A.

A vaccine of the invention can include any of the various DNAs encoding a diphtheria toxoid of the invention, or a cell or virus containing a DNA of the invention, preferably a live vaccine cell, more preferably a *B. subtilis*, BCG, *Salmonella sp.*, *Vibrio cholerae*, Listeriae, Yersiniae, Streptococci, *Corynebacterium diphtheriae*, or *E. coli* cell. A "live vaccine cell", as used herein, is either a naturally avirulent live microorganism, or a live microorganism with either low or attenuated virulence, that expresses an immunogen.

One method for manufacturing a vaccine of the invention includes culturing a cell containing DNA encoding a diphtheria toxoid of the invention under conditions permitting proliferation of the cell, the cell being one that is suitable for introduction into an animal as a live-cell vaccine. The vaccine can be used in a method of immunizing a mammal against diphtheria, preferably a human, the method including introducing an immunizing amount of a vaccine of the invention into the mammal. One, but not the only, method of administering an acellular vaccine that includes a DNA encoding a diphtheria toxoid of the invention is by biolistic transfer, a method of delivery involving coating a microprojectile with DNA encoding an immunogen of interest, and injecting the coated microprojectile directly into cells of the recipient (Tang, et al., Nature 356:152–154, 1992; hereby incorporated by reference). The diphtheria toxoid of the invention is then expressed from the DNA to stimulate an immune response in the recipient. By incorporating immunogens, or DNAs encoding immunogens, that induce an immunologic response against diphtheria toxin, the vaccines of the invention immunize against progression of the disease diphtheria, and against infection by the bacterium *Corynebacterium diphtheriae*.

In another embodiment, the invention features a polypeptide that is an immunologically cross-reactive form of diphtheria toxin Fragment A, or preferably of Fragment A and Fragment B, wherein amino acids corresponding to Val-147 and Glu-148 (SEQ ID NO: 1) of naturally-occurring diphtheria toxin are absent from the polypeptide. Preferably, the toxoid retains Tyr-149. Preferably, a third amino acid residue in the naturally occurring toxin is deleted or is altered to encode an amino acid residue different from the third amino acid residue in the naturally occurring toxin, the presence of the third amino acid residue in the naturally occurring toxin being essential for the full toxic activity of the naturally occurring toxin. The third amino acid residue can be in the Fragment A portion of diphtheria toxin, preferably His-21, Glu-22, Lys-39, Gly-52, Gly-79, Gly-128, Ala-158, or Glu-162, or in the Fragment B portion of diphtheria toxin, preferably amino acid Glu-349, Asp-352, or Ile-364. In addition, Glu-142 of the polypeptide can be absent or altered to an amino acid other than Glu. Alternatively, all of the amino acids from Glu-142 to Glu-148 can be absent. The polypeptide can be made by any suitable method, preferably by culturing any of the various cells containing a DNA encoding a diphtheria toxoid of the invention under conditions permitting the expression of the DNA. Included in the invention is a substantially pure preparation of a polypeptide of the invention. By substantially pure is meant that at least 50% (by weight) of the protein present in the preparation is the diphtheria toxoid polypeptide of the invention. In preferred embodiments, at least 75%, more preferably at least 90%, and most preferably at least 99% (by weight) of the protein present in the preparation is the diphtheria toxoid polypeptide of the invention.

A vaccine against diphtheria toxin can be made of a composition that includes a diphtheria toxoid polypeptide of the invention, and an adjuvant. Adjuvants can include, but are not limited to, any presently known type of adjuvant such as aluminum salts, bacterial endotoxins, Bacillus Calmette-Guerin (BCG), liposomes, microspheres (i.e., microencapsulation polymers used in orally administered vaccines), and Freund's complete or incomplete adjuvant. An "adjuvant", as used herein, is a substance that is capable of increasing the immunogenicity of an antigen.

The diphtheria toxoid polypeptide of the invention may be covalently attached to a moiety, e.g., a polysaccharide or a second polypeptide. The moiety may serve as a carrier substance for the polypeptide; or, alternatively, the diphtheria toxoid polypeptide of the invention can serve as a carrier substance for the moiety, preferably enhancing the immunogenicity of the moiety. A "carrier substance" is a substance that confers stability on, and/or aids or enhances the transport or immunogenicity of, an associated molecule.

A diphtheria toxoid of the invention can also be part of a fusion polypeptide consisting of the diphtheria toxoid polypeptide of the invention linked by a peptide bond to an additional polypeptide. Preferably, the fusion polypeptide is included in a vaccine, which can be used to immunize a human patient against diphtheria toxin. The diphtheria toxoid polypeptide of the invention can act as a carrier substance for the additional polypeptide, preferably enhancing the immunogenicity of that additional polypeptide. The DNA encoding the fusion polypeptide can be used directly as a vaccine, or can be incorporated into a cell, and preferably that cell (e.g. a live vaccine cell), capable of expressing the fusion polypeptide, is used as a vaccine against diphtheria toxin "Fusion polypeptide", as used herein, refers to a protein molecule produced by expression of a hybrid DNA in which a DNA encoding the diphtheria toxoid of the invention is linked by means of genetic engineering to a second DNA encoding a second polypeptide sequence.

"Homology" as applied herein, refers to the sequence identity between two polypeptide molecules or between two nucleic acid molecules. When a given position in both of the two compared sequences is occupied by the same amino acid monomeric subunit, e.g., if a position in each of two polypeptide molecules is occupied by aspartate, then the molecules are homologous at the position. The homology between two sequences is a function of the number of matching positions shared by the two sequences. For example, if 6 of 10 of the positions in two sequences are matched or homologous then the two sequences are 60% homologous. By way of example, the amino acid sequences LTVSFR and LPVSAT share 50% homology. As a preferred embodiment of the invention, an immunologically cross-reactive form of diphtheria toxin Fragment A or Fragment B is at least 40%, preferably 50%, more preferably at least 60%, and most preferably at least 80% homologous to naturally occurring Fragment A or B, respectively.

Applicants have shown how to construct a mutant form of diphtheria toxin Fragment A that is safe to administer to a human patient in the form of a live attenuated vaccine strain which expresses the toxoid of the invention. Use of a live vaccine strain has many advantages over immunizing with a diphtheria toxoid alone. A live organism proliferates in the recipient and expresses the cloned protective protein antigen. A live attenuated vaccine remains in the vaccinee longer than would an injected polypeptide, and continuously produces the genetically engineered protein in situ. Such a live vaccine may require fewer injections or boosters for effective immunization, can often be orally administered, and can be used to administer multiple antigens at once.

To this end, Applicants have experimentally deleted or substituted amino acids in the vicinity of the active site for ADP-ribosyltransferase activity, i.e., amino acids on the $NH_2$-terminal side of Glu-148 of FIG. 1 (SEQ ID NO:1). In so doing, they have determined which amino acid positions, if mutated to a Glu residue, would restore toxic activity to a DT toxoid in which the critical residue Glu-148 is missing. With this knowledge, these residues can be deleted or altered in such a way as to reduce the probability that phenotypic reversion would occur in vivo. In this way, Applicants have designed mutations of diphtheria toxin which render it enzymatically dysfunctional and substantially free of any risk of reversion, even in a continuously proliferating microbial host.

The resulting toxoid, combined with a pharmaceutically suitable vehicle to form a vaccine composition that is inoculated into a mammal, generates immunological protection against diphtheria toxin. The toxoid is produced by culturing a cell that includes a DNA vehicle having DNA encoding the toxoid and regulatory DNA capable of effecting its expression.

Other features and advantages of the invention will be apparent from the following detailed description and from the claims.

DETAILED DESCRIPTION

We first briefly describe the drawings.

Drawings

A study was undertaken of possible second-site mutations in a Glu-148 deletion mutant construct (termed DT delta-148) which might cause reversion to toxicity. It was found that activity can be partially restored by either of two mutations: changing valine-147 to glutamic acid (a two-base change), or deletion of five residues towards the amino-terminus (a fifteen nucleotide deletion), thereby positioning Glu-142 in the position adjacent to Tyr-149. Thus, simply deleting a crucial residue such as Glu-148 cannot insure that a second-site mutation would not restore partial activity to a recombinant toxoid.

This spurred Applicants to construct additional genetic aberrations in DT which would require more extensive mutations to restore toxicity, and thus would be less likely to occur naturally. First, a double amino acid deletion (residues 147, 148) was made at the active-site of DT. This mutation alone renders toxicity of the DT toxoid less than $10^{-4}$ that of wild-type DT with respect to levels of protein synthesis inhibition. Moreover, the appropriate three base change would have to occur in order for residue 146 to mutate to a glutamic acid and restore any detectable activity. Secondly, the isoleucine residue at position 364 was changed to a lysine. This residue is located in the translocation domain and plays an important role in DT's translocation from the endocytic vesicle to the cytosol. Independently, this mutation produces a toxoid that is 500-fold deficient in protein synthesis inhibition compared to wild-type DT. The appropriate two base change would have to occur in order for lysine 364 to mutate to isoleucine and restore toxicity.

EXPERIMENTAL INFORMATION

Methods

Preparation and Analysis of Mutant Diphtheria Toxoids

Deletions and substitutions can be generated by oligo-nucleotide-directed mutagenesis of the diphtheria toxin Fragment A (DTA) gene, as described below. The mutant genes can then be expressed in *E. coli* or any other standard expression system by standard methods, and extracts assayed for NAD:EF-2 ADP-ribosyltransferase activity and for DT-specific protein by Western blot analysis as described below.

EXAMPLE

A plasmid encoding the F2 fragment of DT, pBRp-tacBamHIATGF2, was constructed according to the method of Greenfield et al. (Greenfield et al., *PNAS.* 80:6853–6857, 1983). The F2 fragment of DT contains the naturally-occurring DT leader sequence, all of Fragment A, and the N-terminal 189 amino acid residues of Fragment B, so that the final construct includes amino acids 1–382 of SEQ ID NO:1.

The plasmid F2 was digested with BamHI and ClaI. The resulting 949 base-pair fragment was ligated with BamHI- and AccI-restricted M13mp19, yielding M13mp19-F2. An NdeI restriction site spanning the translational start codon of F2, and a translational stop codon at Arg-192 of F2 were created by the site-directed mutagenesis procedure described by Sayers et al. (*Nucleic Acids Res.* 16:791, 1988), yielding M13mp19-DTA. The 968 base-pair NdeI-HindIII fragment of M13mp19-DTA was ligated in NdeI- and HindIII-restricted pT7-7 (Tabor, in *Current Protocols in Molecular Biology,* Ausubel et al., eds.; Greene, Wiley-Interscience, New York, 1991, pages 16.2.1–16.2.11), and the resulting plasmid, pT7-DTA, was used as a cloning vector to prepare each of the site-directed mutagenesis constructs of DTA listed in Table 1. All site-directed mutants were constructed with M13mp19-DTA template DNA and the appropriate oligonucleotide. The 539-base-pair ApaI-BalI restricted fragment of M13mp19-DTA, which encompassed the appropriate active-site mutation, was ligated with ApaI- and BalI-restricted pT7-DTA and used to transform competent *E. coli* BL21(DE3) (Studier et al., *J. Mol. Biol.* 189:113, 1986). Transformants were grown overnight in Luria broth (100 µg/ml ampicillin), diluted 1/50 in M9 minimal media (100 µg/ml ampicillin), grown to OD 1.0, induced for 3 hours with 1 mM IPTG, and harvested by centrifugation (3000×g, 5 min). Cell pellets were resuspended in 1/30 volume 10 mM Tris, 1 mM EDTA, pH 8.0 (TE)+5 mM $CaCl_2$, 5 mM $MgCl_2$; freeze-thaw cycled three times; incubated for 15 min with 0.1 mg/ml lysozyme and 1 µg/ml DNAseI; clarified by centrifugation (10,000×g, 10 min) and desalted on G-25 Sephadex, as described earlier (Douglas et al., *J. Bacteriol.* 169:4967, 1987). DTA-protein was then measured by Western blot analysis and ADP-ribosyltransferase activity was assayed as described (Tweten et al., *J. Biol. Chem.* 260:10392, 1985). Construction of full-length diphtheria toxin delta147,148;364I>K and delta146–148;364I>K.

PT7-DTA delta147,148 and PT7-DTA delta146–148 were digested with ApaI, MscI. The 539 bp ApaI-MscI fragment spanning each active-site deletion was isolated from a 1% agarose gel and ligated separately into ApaI, MscI digested ptac DT Ser148;364I>K, yielding ptacDTdelta147, 148;364I>K and ptacDTdelta146–148;364I>K. Each plasmid was used to transform competent *E. coli* TG-1. Transformants were grown overnight in Luria broth +100 µg/ml ampicillin (L-amp), diluted 1/50 in L-amp. grown to OD 1.0, induced for 3 h with IPTG, and harvested by centrifugation (3000×g, 5 min). Cell pellets were resuspended in 1/30 volume 10 mM Tris, 1 mM EDTA, pH 8.0 (TE)+5 mM $CaCl_2$, 5 mM $MgCl_2$; freeze-thaw cycled three times; incubated for 15 min with 0.1 mg/ml lysozyme and 1 µg/ml DNAseI; clarified by centrifugation (10,000×g, 10 min) and desalted on G-50 Sephadex, by the same method used to desalt with G-25 Sephadex, as cited above.

Results

After deletion of Glu-148 (Table 1, Mutation 1), the specific NAD:EF-2 ADP-ribosyltransferase activity of the resulting mutant form of DTA was undetectable (less than $10^{-4}$ that of wild-type DTA.) However, this deletion, when combined with the replacement of Val-147 by a Glu residue, created a product with 6% wild-type activity (Table 1, Mutation 7). In contrast, deletion of Glu-148 coupled with a Tyr-149 to Glu mutation (Table 1, Mutation 12) yielded an inactive product.

Longer deletions extending from Glu-148 $NH_2$-terminally as far as residue 144 (Table 1, Mutations 2–5) yielded products with no detectable ADP-ribosylation activity. However, the next construct in this series (Table 1, Mutation 6), involving deletion of residues 143–148 inclusive, produced a protein with detectable (0.6% of wild-type) activity. In Mutation 6, unlike Mutations 1–5, the $NH_2$-proximal residue flanking the deletion is a glutamic acid (Glu-142). Activity ranging between 0.6% and 9% that of wild-type DTA was observed when each deletion (Mutations 1–5) was combined with substitution of the $NH_2$-proximal flanking residue with Glu (Table 1, Mutations 7–11).

Full-length diphtheria toxin constructs possessing specific active-site deletions plus the addition of a membrane translocation domain modification were also assessed for overall protein stability. Western blot analysis of both full-length diphtheria toxin constructs (delta147,148;364I>K and delta146–148;364I>K) revealed a single full-length protein band with few degradation products suggesting that the structural integrity of the protein was preserved.

Figure 2:
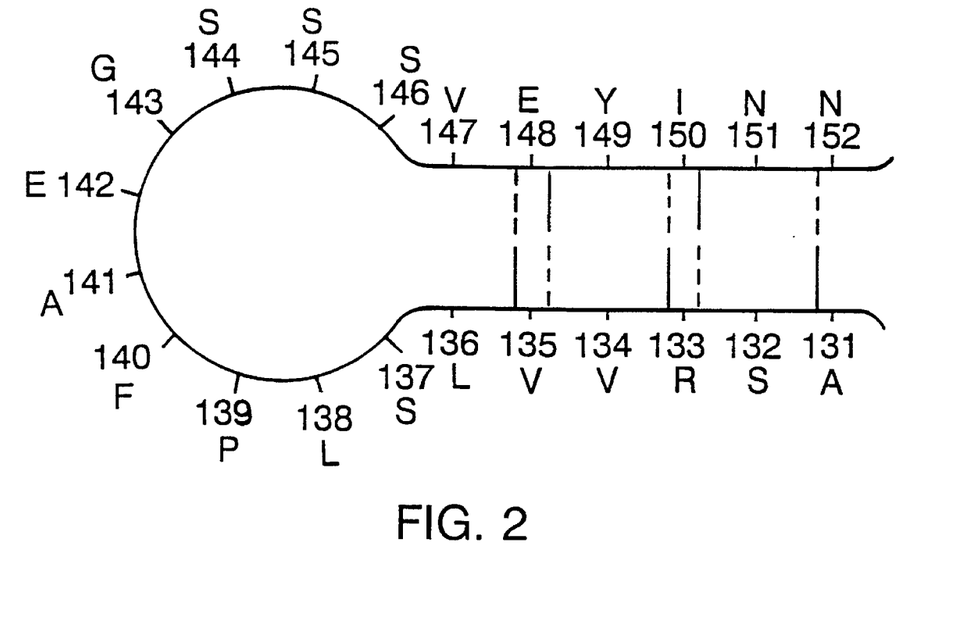
FIG. 2 is a schematic representation of the secondary structure within which Glu-148 resides. The drawing is based on the previously described x-ray crystallographic model of the DT dimer (Collier et al., U.S. Ser. No. 07/881,394, herein incorporated by reference; Choe et al., *Nature* 357:216–222, 1992). Glu-148 (E148) is seen to lie on a β-strand, one residue removed from a loop connecting this strand with the adjacent, $NH_2$-proximal β-strand. H-bonds between backbone N (- - -) and carbonyl O (—) atoms within these 2 strands are shown.

These active-site mutation results are consistent with a model in which the local polypeptide on the $NH_2$-proximal flank of Glu-148 is more flexible and less firmly anchored than the local peptide on the COOH-proximal flank. The x-ray crystallographic structure of the DT dimer (Collier et al., U.S. Ser. No. 07/881,394) provides support for this model. Glu-148 resides within an antiparallel β-sheet bounding the active-site cleft and is only one residue removed from a large, 10-residue loop (residues 137–146), which connects the Glu-148 β-strand to the adjacent, $NH_2$-proximal β-strand (FIG. 2). The polypeptide backbone of the four residues immediately following Glu-148 (residues 149–152) is involved in H-bonding typical of antiparallel β-sheet, and this bonding, together with other packing interactions, may firmly anchor this region of polypeptide within the protein.

These results illustrate two discrete genetic changes, one involving a substitution and the other an additional deletion, each of which is capable of reverting an enzymatically inactive diphtheria toxin active-site deletion mutant to a partially toxic state. The levels of activity restored are in all cases less than 10% of wild-type, but are clearly of concern if the protein is to be expressed in vivo by a live vaccine. The substitution of Glu for Val-147 could occur by either of two possible two base-pair transversions of the Val codon (GTT) to a Glu codon (GAA or GAG). In contrast, deletion of both the Val-147 codon and the Glu-148 codon leaves Ser-146 immediately adjacent to Tyr-149; since the Ser AGC codon cannot be converted into a Glu codon without a change in all three nucleotides, the risk of reversion of this particular six-nucleotide deletion mutant to a mutant with some restored activity is substantially less (a probability lower than $10^{-10}$/cell/generation) than the risk of reversion of the mutant lacking only the Glu-148 codon.

Moreover, the construction of a genetic diphtheria toxoid possessing both an active-site deletion and another, independent aberration (membrane translocation dysfunction) further reduces the risk of reversion to toxicity. Either DT delta147,148 or delta146–148 coupled with 364I>K would require the appropriate five base change (three at residue 146 or 145 and two at residue 364) to restore detectable toxicity.

This recombinant toxoid, DT delta147,148;364I>K was cloned, expressed in *E. coli,* and assessed for overall protein stability and ADP-ribosyltransferase activity. Western blot analysis revealed a single full-length protein with few degradation products suggesting that the stability and overall structural integrity of the protein was maintained. As anticipated, the recombinant toxoid was devoid of activity ($<10^{-4}$ that of wild-type toxin).

Immunogenicity

After confirming that the mutant protein so produced lacks detectable enzymatic activity, the mutants may then be analyzed for immunogenicity as follows:

Guinea pigs (or another species which is naturally sensitive to the cell-killing effects of diphtheria toxin) are immunized with the recombinant toxoid of the invention according to the following protocol: between 1 and 50 μg recombinant toxoid, suspended in 50–100 μl of Freud's complete adjuvant, is subcutaneously injected into a guinea pig on day 1, day 12, and day 24. Blood samples are then assayed for antitoxin antibodies by testing serial dilutions for reactivity to naturally occurring diphtheria toxin. Those animals which received high enough doses of toxoid to induce antitoxoid formation can be challenged with wild type diphtheria toxin, in order to see whether the antibodies are protective. Those toxoids of the invention which induce a positive response in the above assay are likely candidates for incorporation into live vaccines.

Appropriate live vaccine microorganisms (cells or viruses) genetically engineered to express a toxoid of the invention can be tested by injecting the candidate vaccine into a DT sensitive animal, and, after a 2–3 month incubation period, challenging the animal with either a) a lethal dose of naturally occurring DT, or b) multiple, serially administered doses of naturally occurring DT, so as to calibrate the range of acquired immunity.

Preparation and Use of a DNA encoding a Diphtheria Toxoid

A DNA sequence encoding the diphtheria toxoid of the invention can be expressed by standard methods in a prokaryotic host cell. DNA encoding the diphtheria toxoid of the invention is carried on a vector operably linked to control signals capable of effecting expression in the prokaryotic host. If desired, the coding sequence can contain, at its 5' end, a sequence encoding any of the known signal sequences capable of effecting secretion of the expressed protein into the periplasmic space of the host cell, thereby facilitating recovery of the protein. By way of example, a vector expressing the diphtheria toxoid of the invention, or a fusion protein including the polypeptide of the invention, can consist of (i) an origin of replication functional in *E. coli* derived from the plasmid pBR322; (ii) a selectable tetracycline resistance gene also derived from pBR322; (iii) a transcription termination region, e.g., the termination of the *E. coli* trp operon (placed at the end of the tetracycline resistance gene to prevent transcriptional readthrough into the trp promoter region); (iv) a transcription promoter, e.g., the trp operon promoter, or the diphtheria toxin promoter; (v) the protein coding sequence of the invention; and (vi) a transcription terminator, e.g., the T1T2 sequence from the ribosomal RNA (rrnB) locus of *E. coli*. The sequences of carrier molecules, the methods used in the synthesis of the DNA sequences, the construction of fusion genes, and the appropriate vectors and expression systems are all well known to those skilled in the art. Similar expression systems can be designed for fusion or non-fusion polypeptides, i.e., for expression of the polypeptide of the invention alone. These procedures are an example of, but are not limiting on, the methods of the invention.

Prokaryotes most frequently used are represented by various strains of *E. coli*; however, other microbial strains can also be used, e.g., *C. diphtheriae*. Plasmid vectors are used which contain replication origins, selectable markers, and control sequences derived from a species compatible with the microbial host. For example, *E. coli* can be transformed using derivatives of pBR322, a plasmid constructed by Bolivar, et al. (Gene 2:95, 1977) using fragments derived from three naturally-occurring plasmids, two isolated from species of Salmonella, and one isolated from *E. coli*. pBR322 contains genes for ampicillin and tetracycline resistance, and thus provides multiple selectable markers which can be either retained or destroyed in constructing the desired expression vector. Commonly used prokaryotic expression control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., *Nature* 198:1056, 1977) and the tryptophan (trp) promoter systems (Goeddel et al., *Nucl. Acids Res.* 8:4057, 1980) as well as the lambda-derived $P_L$ promoter and N-gene ribosome binding site (Shimatake et al., *Nature* 292:128, 1981). Examples of microbial strains, vectors, and associated regulatory sequences are listed herein to illustrate, but not to limit, the invention.

Preparation and Use of a Polypeptide Vaccine

The mutant diphtheria toxoid of the invention can be expressed in any known protein expression system and then purified by standard means. For instance, diphtheria toxoids of the invention can be synthesized by organic chemical synthesis or produced as a biosynthesized polypeptide. Organic chemical synthesis can be performed by conventional methods of automated peptide synthesis, or by classical organic chemical techniques. One schooled in the art can purify the diphtheria toxoid polypeptide of the invention using conventional methods of protein isolation, e.g., methods including but not limited to precipitation, chromatography, immunoadsorption, or affinity techniques. The polypeptide can be purified from the cells, or medium of the cells, of a microbial strain genetically engineered to express the diphtheria toxoid of the invention.

The purified polypeptide may be combined with a suitable carrier (such as physiological saline); with an adjuvant that increases the immunogenicity of the toxoid (such as aluminum salts, bacterial endotoxins or attenuated bacterial strains (e.g., BCG or *Bordetella pertussis*), attenuated viruses, liposomes, microspheres, or Freud's complete or incomplete adjuvant)); and/or with additional toxoids or killed or attenuated vaccine organisms (to form a multivalent vaccine). Such a vaccine may then be administered to a human subject by any acceptable method, including but not limited to oral, parenteral, transdermal and transmucosal delivery. Administration can be in a sustained release formulation using a biodegradable biocompatible polymer, such as a microsphere, by on-site delivery using micelies, gels or liposomes, or by transgenic modes (e.g., by biolistic administration of the DNA of the invention directly into the patient's cells, as described by Tang et al., *Nature* 356:152–154, 1992, herein incorporated by reference).

Preparation and Use of Live Recombinant Vaccines

Appropriate live carrier organisms include attenuated microorganisms such as BCG, *Salmonella sp.*, *Vibrio cholerae*, Streptococci, Listeriae, and Yersiniae. The DNA of the invention can be stably transfected into such a microbial strain by standard methods (Sambrook et al., *Molecular*

Cloning: A Laboratory Manual. Cold Spring Harbor Lab. Press, New York, 1989.), and then would be introduced into a patient by, for example, oral or parenteral administration. Once introduced into the patient, the bacterium would multiply and express the mutant form of diphtheria toxin within the patient, causing the patient to maintain a protective level of antibodies to the mutant toxin. In a similar manner, an attenuated animal virus such as adenovirus, herpes virus, vaccinia virus, polio, fowl pox, or even attenuated eukaryotic parasites such as Leishmania may be employed as the carrier organism. The mutant DNA of the invention can be incorporated by genetic engineering techniques into the genome of any appropriate virus, which is then introduced into a human vaccinee by standard methods. A live vaccine of the invention can be administered at, for example, about $10^4$–$10^8$ organisms/dose, or a dose that is sufficient to stably induce protective levels of antitoxin.

can be generated which lacks Glu-142 as well as Val-147 and Glu-148, or which lacks all of the residues from Glu-142 to Glu-148, inclusive. Such deletion mutants can be generated by site directed mutagenesis (Sayers, et al., supra), and analyzed for enzymatic activity and immunogenicity as described above. Other amino acid residues that have been shown to be essential for the biological activity of diphtheria toxin include residues His-21, Glu-22, Lys-39, Gly-52, Gly-79, Gly-128, Ala-158, and Gly-162 of the Fragment A portion of diphtheria toxin, and residues Glu-349, Asp-352, and Ile-364 of the Fragment B portion. Mutants lacking any one or more of these residues, in addition to lacking both Val-147 and Glu-148, may be generated by standard methods of site-directed mutagenesis known to one schooled in the art.

TABLE 1

ADP-ribosyltransferase activities of diphtheria toxin A-fragment with active-site mutations

| Mutation | 141 Ala | 142 Glu | 143 Gly | 144 Ser | 145 Ser | 146 Ser | 147 Val | 148 Glu | 149 Tyr | Activity |
|---|---|---|---|---|---|---|---|---|---|---|
| None |  |  |  |  |  |  |  |  |  | 100% |
| 1 |  |  |  |  |  |  |  | —* |  | ND** |
| 2 |  |  |  |  |  |  | — | — |  | ND |
| 3 |  |  |  |  |  | — | — | — |  | ND |
| 4 |  |  |  |  | — | — | — | — |  | ND |
| 5 |  |  |  | — | — | — | — | — |  | ND |
| 6 |  |  | — | — | — | — | — | — |  | 0.6% |
| 7 |  |  |  |  |  |  | Glu | — |  | 6% |
| 8 |  |  |  |  |  | Glu | — | — |  | 9% |
| 9 |  |  |  |  | Glu | — | — | — |  | 6% |
| 10 |  |  |  | Glu | — | — | — | — |  | 0.6% |
| 11 |  |  | Glu | — | — | — | — | — |  | 4% |
| 12 |  |  |  |  |  |  |  | — | Glu | ND |

*— indicates deleted residue
**ND indicates less than $10^{-4}$ wild-type activity Actual dosages of such a vaccine can be readily determined by one of ordinary skill in the field of vaccine technology.

Cell-Killing Assay

Standard methods of assaying the toxicity of diphtheria toxin mutants employ a diphtheria toxin-sensitive tissue culture cell line, which is a line of cells bearing the diphtheria toxin receptor, e.g., viro or BSC1 cells. The cells are treated with a known amount of the candidate mutant diphtheria toxin, with naturally occurring diphtheria toxin (as a positive control), or with bovine serum albumin (as a negative control). After incubation, a survival assay is performed by counting viable colonies (Yamaizumi, M. et al. Cell 15:245–250, 1978). Alternatively, the extent of cell-killing can be determined by measuring the extent of inhibition of protein synthesis. After incubation with one of the diphtheria toxin samples described above, a radiolabelled amino acid (e.g., [$^{14}$C]Leu) is added to the growth medium of the cell culture, and the decline in de novo protein synthesis is measured by scintillation counting of TCA-precipitable protein. Such methods are routine, and known to one skilled in the art.

OTHER EMBODIMENTS

Other embodiments are within the claims set forth below. For example, a mutant form of diphtheria toxin Fragment A

What is claimed is:

1. A DNA encoding an immunologically cross-reactive form of diphtheria toxin Fragment A, wherein the codons corresponding to Val-147 and Glu-148 of naturally-occurring diphtheria toxin (FIG. 1; SEQ ID NO:1) are absent from said DNA.

2. The DNA of claim 1, wherein said DNA further comprises a nucleic acid sequence encoding part or all of diphtheria toxin Fragment B.

3. The DNA of claim 1, wherein the codon corresponding to Glu-142 (FIG. 1; SEQ ID NO:1) is absent or is altered to encode an amino acid other than Glu.

4. The DNA of claim 3, wherein all of the codons from Glu-142 to Glu-148 (FIG. 1; SEQ ID NO:1) are absent.

5. The DNA of claim 1, wherein a codon corresponding to a third amino acid residue of said naturally occurring toxin is deleted or is altered to encode an amino acid residue different from said third amino acid residue of said naturally occurring toxin, the presence of said third amino acid residue of said naturally occurring toxin being essential for the full toxic activity of said naturally occurring toxin, said third amino acid residue being selected from the group consisting of His-21, Glu-22, Lys-39, Gly-52, Gly-79, Gly-128, Glu-142, Gly-143, Ser-144, Ser-145, Ser-146, Ala-158, Glu-162, Glu-349, Asp-352, and Ile-364 (FIG. 1; SEQ ID NO:1).

6. The DNA of claim 1, wherein said DNA includes a codon encoding Tyr-149 of naturally occurring diphtheria toxin.

7. A cell comprising the DNA of claim 1.

8. The cell of claim 7, wherein said cell is a *B. subtilis*, Bacillus Calmette-Guerin (BCG), *Salmonella sp.*, *Vibrio cholerae*, Listeriae, Yersiniae, Streptococci, *Corynebacterium diphtheriae*, or an *E. coli* cell.

9. A vaccine comprising a prokaryotic cell containing the DNA of claim 5.

10. A vaccine comprising the cell of claim 7, wherein said cell is a prokaryote.

11. A method of using the DNA of claim 1 to prepare an immunologically cross-reactive form of diphtheria toxin Fragment A, wherein Val-147 and Glu-148 of naturally-occurring diphtheria toxin are absent, which method comprises culturing a cell comprising said DNA under conditions permitting the expression of said DNA.

12. A method of using the DNA of claim 1 in a vaccine, which method comprises culturing a prokaryotic cell comprising said DNA under conditions permitting proliferation of said cell, wherein said cell is suitable for introduction into an animal as a live-cell vaccine.

13. A method for immunizing a mammal against diphtheria, which method comprises introducing an immunizing amount of a vaccine made by the method of claim 12.

14. The method of claim 13, wherein said mammal is a human.

15. A method for immunizing a mammal against diphtheria, which method comprises introducing an immunizing amount of the vaccine of claim 10 into said mammal.

16. A DNA encoding a fusion polypeptide, wherein the DNA of claim 1 is fused in frame to a DNA encoding a second polypeptide.

17. A cell comprising the DNA of claim 16.

18. A vaccine comprising a prokaryotic cell comprising the DNA of claim 16.

19. A method of immunizing a human patient against diphtheria toxin comprising administering to a patient an immunogenically effective amount of the vaccine of claim 18.

* * * * *

UNITED STATES PATENT AND TRADEMARK OFFICE
CERTIFICATE OF CORRECTION

PATENT NO. : 5,601,827

DATED : February 11, 1997

INVENTOR(S) : Collier et al.

It is certified that error appears in the above-identified patent and that said Letters Patent is hereby corrected as shown below:

```
Column 4, line 19, change "Glu-22" to --Gly-22--;
Column 12, line 9, change "Glu-22" to --Gly-22--; and
    Column 17, line 31, change "Glu-22" to --Gly-22--.
```

Signed and Sealed this

Seventh Day of March, 2000

Attest:

Attesting Officer

Q. TODD DICKINSON

Commissioner of Patents and Trademarks

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
        ( A ) LENGTH: 1942
        ( B ) TYPE: nucleic acid
        ( C ) STRANDEDNESS: double
        ( D ) TOPOLOGY: linear     ( x i ) SEQUENCE DESCRIPTION: SEQ ID NO: 1:

```
CCGGCGTTGC GTATCCAGTG GCTACACTCA GGTTGTAATG ATTGGGATGA TGTACCTGAT      60

CTGAGAGCGA TTAAAAACTC ATTGAGGAGT AGGTCCCGAT TGGTTTTTGC TAGTGAAGCT     120

TAGCTAGCTT TCCCCATGTA ACCAATCTAT CAAAAAGGG  CATTGATTTC AGAGCACCCT     180

TATAATTAGG ATAGCTTTAC CTAATTATTT TATGAGTCCT GGTAAGGGGA TACGTTGTGA     240

GCAGAAAACT GTTTGCGTCA ATCTTAATAG GGGCGCTACT GGGGATAGGG GCCCCACCTT     300

CAGCCCATGC A                                                         311
```

```
GGC GCT GAT GAT GTT GTT GAT TCT TCT AAA TCT TTT GTG ATG GAA AAC       359
Gly Ala Asp Asp Val Val Asp Ser Ser Lys Ser Phe Val Met Glu Asn
1               5                   10                  15

TTT TCT TCG TAC CAC GGG ACT AAA CCT GGT TAT GTA GAT TCC ATT CAA       407
Phe Ser Ser Tyr His Gly Thr Lys Pro Gly Tyr Val Asp Ser Ile Gln
            20                  25                  30

AAA GGT ATA CAA AAG CCA AAA TCT GGT ACA CAA GGA AAT TAT GAC GAT       455
Lys Gly Ile Gln Lys Pro Lys Ser Gly Thr Gln Gly Asn Tyr Asp Asp
        35                  40                  45

GAT TGG AAA GGG TTT TAT AGT ACC GAC AAT AAA TAC GAC GCT GCG GGA       503
Asp Trp Lys Gly Phe Tyr Ser Thr Asp Asn Lys Tyr Asp Ala Ala Gly
    50                  55                  60

TAC TCT GTA GAT AAT GAA AAC CCG CTC TCT GGA AAA GCT GGA GGC GTG       551
Tyr Ser Val Asp Asn Glu Asn Pro Leu Ser Gly Lys Ala Gly Gly Val
65                  70                  75                  80

GTC AAA GTG ACG TAT CCA GGA CTG ACG AAG GTT CTC GCA CTA AAA GTG       599
Val Lys Val Thr Tyr Pro Gly Leu Thr Lys Val Leu Ala Leu Lys Val
                85                  90                  95

GAT AAT GCC GAA ACT ATT AAG AAA GAG TTA GGT TTA AGT CTC ACT GAA       647
Asp Asn Ala Glu Thr Ile Lys Lys Glu Leu Gly Leu Ser Leu Thr Glu
            100                 105                 110

CCG TTG ATG GAG CAA GTC GGA ACG GAA GAG TTT ATC AAA AGG TTC GGT       695
Pro Leu Met Glu Gln Val Gly Thr Glu Glu Phe Ile Lys Arg Phe Gly
        115                 120                 125

GAT GGT GCT TCG CGT GTA GTG CTC AGC CTT CCC TTC GCT GAG GGG AGT       743
Asp Gly Ala Ser Arg Val Val Leu Ser Leu Pro Phe Ala Glu Gly Ser
    130                 135                 140

TCT AGC GTT GAA TAT ATT AAT AAC TGG GAA CAG GCG AAA GCG TTA AGC       791
Ser Ser Val Glu Tyr Ile Asn Asn Trp Glu Gln Ala Lys Ala Leu Ser
145                 150                 155                 160

GTA GAA CTT GAG ATT AAT TTT GAA ACC CGT GGA AAA CGT GGC CAA GAT       839
Val Glu Leu Glu Ile Asn Phe Glu Thr Arg Gly Lys Arg Gly Gln Asp
                165                 170                 175

GCG ATG TAT GAG TAT ATG GCT CAA GCC TGT GCA GGA AAT CGT GTC AGG       887
Ala Met Tyr Glu Tyr Met Ala Gln Ala Cys Ala Gly Asn Arg Val Arg
            180                 185                 190

CGA TCA GTA GGT AGC TCA TTG TCA TGC ATA AAT CTT GAT TGG GAT GTC       935
Arg Ser Val Gly Ser Ser Leu Ser Cys Ile Asn Leu Asp Trp Asp Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 195 |     |     |     |     | 200 |     |     |     |     |     | 205 |     |     |     |      |
| ATA | AGG | GAT | AAA | ACT | AAG | ACA | AAG | ATA | GAG | TCT | TTG | AAA | GAG | CAT | GGC | 983  |
| Ile | Arg | Asp | Lys | Thr | Lys | Thr | Lys | Ile | Glu | Ser | Leu | Lys | Glu | His | Gly |      |
|     | 210 |     |     |     | 215 |     |     |     |     | 220 |     |     |     |     |     |      |
| CCT | ATC | AAA | AAT | AAA | ATG | AGC | GAA | AGT | CCC | AAT | AAA | ACA | GTA | TCT | GAG | 1031 |
| Pro | Ile | Lys | Asn | Lys | Met | Ser | Glu | Ser | Pro | Asn | Lys | Thr | Val | Ser | Glu |      |
| 225 |     |     |     | 230 |     |     |     |     | 235 |     |     |     |     |     | 240 |      |
| GAA | AAA | GCT | AAA | CAA | TAC | CTA | GAA | GAA | TTT | CAT | CAA | ACG | GCA | TTA | GAG | 1079 |
| Glu | Lys | Ala | Lys | Gln | Tyr | Leu | Glu | Glu | Phe | His | Gln | Thr | Ala | Leu | Glu |      |
|     |     |     |     | 245 |     |     |     |     | 250 |     |     |     |     | 255 |     |      |
| CAT | CCT | GAA | TTG | TCA | GAA | CTT | AAA | ACC | GTT | ACT | GGG | ACC | AAT | CCT | GTA | 1127 |
| His | Pro | Glu | Leu | Ser | Glu | Leu | Lys | Thr | Val | Thr | Gly | Thr | Asn | Pro | Val |      |
|     |     |     |     | 260 |     |     |     |     | 265 |     |     |     | 270 |     |     |      |
| TTC | GCT | GGG | GCT | AAC | TAT | GCG | GCG | TGG | GCA | GTA | AAC | GTT | GCG | CAA | GTT | 1175 |
| Phe | Ala | Gly | Ala | Asn | Tyr | Ala | Ala | Trp | Ala | Val | Asn | Val | Ala | Gln | Val |      |
|     |     | 275 |     |     |     |     | 280 |     |     |     |     | 285 |     |     |     |      |
| ATC | GAT | AGC | GAA | ACA | GCT | GAT | AAT | TTG | GAA | AAG | ACA | ACT | GCT | GCT | CTT | 1223 |
| Ile | Asp | Ser | Glu | Thr | Ala | Asp | Asn | Leu | Glu | Lys | Thr | Thr | Ala | Ala | Leu |      |
|     |     | 290 |     |     |     |     | 295 |     |     |     |     | 300 |     |     |     |      |
| TCG | ATA | CTT | CCT | GGT | ATC | GGT | AGC | GTA | ATG | GGC | ATT | GCA | GAC | GGT | GCC | 1271 |
| Ser | Ile | Leu | Pro | Gly | Ile | Gly | Ser | Val | Met | Gly | Ile | Ala | Asp | Gly | Ala |      |
| 305 |     |     |     |     | 310 |     |     |     |     | 315 |     |     |     |     | 320 |      |
| GTT | CAC | CAC | AAT | ACA | GAA | GAG | ATA | GTG | GCA | CAA | TCA | ATA | GCT | TTA | TCG | 1319 |
| Val | His | His | Asn | Thr | Glu | Glu | Ile | Val | Ala | Gln | Ser | Ile | Ala | Leu | Ser |      |
|     |     |     |     | 325 |     |     |     |     | 330 |     |     |     |     | 335 |     |      |
| TCT | TTA | ATG | GTT | GCT | CAA | GCT | ATT | CCA | TTG | GTA | GGA | GAG | CTA | GTT | GAT | 1367 |
| Ser | Leu | Met | Val | Ala | Gln | Ala | Ile | Pro | Leu | Val | Gly | Glu | Leu | Val | Asp |      |
|     |     |     | 340 |     |     |     |     | 345 |     |     |     |     | 350 |     |     |      |
| ATT | GGT | TTC | GCT | GCA | TAT | AAT | TTT | GTA | GAG | AGT | ATT | ATC | AAT | TTA | TTT | 1415 |
| Ile | Gly | Phe | Ala | Ala | Tyr | Asn | Phe | Val | Glu | Ser | Ile | Ile | Asn | Leu | Phe |      |
|     |     | 355 |     |     |     |     | 360 |     |     |     |     | 365 |     |     |     |      |
| CAA | GTA | GTT | CAT | AAT | TCG | TAT | AAT | CGT | CCC | GCG | TAT | TCT | CCG | GGG | CAT | 1463 |
| Gln | Val | Val | His | Asn | Ser | Tyr | Asn | Arg | Pro | Ala | Tyr | Ser | Pro | Gly | His |      |
|     | 370 |     |     |     |     | 375 |     |     |     |     | 380 |     |     |     |     |      |
| AAA | ACG | CAA | CCA | TTT | CTT | CAT | GAC | GGG | TAT | GCT | GTC | AGT | TGG | AAC | ACT | 1511 |
| Lys | Thr | Gln | Pro | Phe | Leu | His | Asp | Gly | Tyr | Ala | Val | Ser | Trp | Asn | Thr |      |
| 385 |     |     |     |     | 390 |     |     |     |     | 395 |     |     |     |     | 400 |      |
| GTT | GAA | GAT | TCG | ATA | ATC | CGA | ACT | GGT | TTT | CAA | GGG | GAG | AGT | GGG | CAC | 1559 |
| Val | Glu | Asp | Ser | Ile | Ile | Arg | Thr | Gly | Phe | Gln | Gly | Glu | Ser | Gly | His |      |
|     |     |     |     | 405 |     |     |     |     | 410 |     |     |     |     | 415 |     |      |
| GAC | ATA | AAA | ATT | ACT | GCT | GAA | AAT | ACC | CCG | CTT | CCA | ATC | GCG | GGT | GTC | 1607 |
| Asp | Ile | Lys | Ile | Thr | Ala | Glu | Asn | Thr | Pro | Leu | Pro | Ile | Ala | Gly | Val |      |
|     |     |     | 420 |     |     |     |     | 425 |     |     |     |     | 430 |     |     |      |
| CTA | CTA | CCG | ACT | ATT | CCT | GGA | AAG | CTG | GAC | GTT | AAT | AAG | TCC | AAG | ACT | 1655 |
| Leu | Leu | Pro | Thr | Ile | Pro | Gly | Lys | Leu | Asp | Val | Asn | Lys | Ser | Lys | Thr |      |
|     |     | 435 |     |     |     |     | 440 |     |     |     |     | 445 |     |     |     |      |
| CAT | ATT | TCC | GTA | AAT | GGT | CGG | AAA | ATA | AGG | ATG | CGT | TGC | AGA | GCT | ATA | 1703 |
| His | Ile | Ser | Val | Asn | Gly | Arg | Lys | Ile | Arg | Met | Arg | Cys | Arg | Ala | Ile |      |
|     | 450 |     |     |     |     | 455 |     |     |     |     | 460 |     |     |     |     |      |
| GAC | GGT | GAT | GTA | ACT | TTT | TGT | CGC | CCT | AAA | TCT | CCT | GTT | TAT | GTT | GGT | 1751 |
| Asp | Gly | Asp | Val | Thr | Phe | Cys | Arg | Pro | Lys | Ser | Pro | Val | Tyr | Val | Gly |      |
| 465 |     |     |     |     | 470 |     |     |     |     | 475 |     |     |     |     | 480 |      |
| AAT | GGT | GTG | CAT | GCG | AAT | CTT | CAC | GTG | GCA | TTT | CAC | AGA | AGC | AGC | TCG | 1799 |
| Asn | Gly | Val | His | Ala | Asn | Leu | His | Val | Ala | Phe | His | Arg | Ser | Ser | Ser |      |
|     |     |     |     | 485 |     |     |     |     | 490 |     |     |     |     | 495 |     |      |
| GAG | AAA | ATT | CAT | TCT | AAT | GAA | ATT | TCG | TCG | GAT | TCC | ATA | GGC | GTT | CTT | 1847 |
| Glu | Lys | Ile | His | Ser | Asn | Glu | Ile | Ser | Ser | Asp | Ser | Ile | Gly | Val | Leu |      |
|     |     |     | 500 |     |     |     |     | 505 |     |     |     |     | 510 |     |     |      |
| GGG | TAC | CAG | AAA | ACA | GTA | GAT | CAC | ACC | AAG | GTT | AAT | TCT | AAG | CTA | TCG | 1895 |
| Gly | Tyr | Gln | Lys | Thr | Val | Asp | His | Thr | Lys | Val | Asn | Ser | Lys | Leu | Ser |      |

| | 515 | | | | 520 | | | 525 | | | |
|---|---|---|---|---|---|---|---|---|---|---|---|
| CTA | TTT | TTT | GAA | ATC | AAA | AGC | TGAAAGGTAG | TGGGGTCGTG | TGCCGG | | 1942 |
| Leu | Phe | Phe | Glu | Ile | Lys | Ser | | | | | |
| | | 530 | | | | 535 | | | | | |